United States Patent
Ayon et al.

(10) Patent No.: US 8,502,679 B2
(45) Date of Patent: Aug. 6, 2013

(54) NONINVASIVE MOTION AND RESPIRATION MONITORING SYSTEM

(75) Inventors: Arturo A. Ayon, San Antonio, TX (US); Christopher Berg, Arlington, TX (US); David C. Valdez, Eagle Pass, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 608 days.

(21) Appl. No.: 12/576,230

(22) Filed: Oct. 8, 2009

(65) Prior Publication Data
US 2010/0109875 A1    May 6, 2010

Related U.S. Application Data

(60) Provisional application No. 61/195,512, filed on Oct. 8, 2008.

(51) Int. Cl.
*G08B 23/00* (2006.01)
(52) U.S. Cl.
USPC ............ 340/573.1; 340/384.7; 340/407.1; 340/539.1; 340/691.6; 600/301
(58) Field of Classification Search
USPC ............ 340/573.1, 539.12, 539.1, 407.1, 340/384.7, 691.4–691.6; 600/534–536, 301, 600/508
See application file for complete search history.

(56) References Cited

U.S. PATENT DOCUMENTS

| | | | | |
|---|---|---|---|---|
| 4,730,604 | A * | 3/1988 | Boggs | 601/55 |
| 5,002,060 | A * | 3/1991 | Nedivi | 600/535 |
| 5,271,412 | A | 12/1993 | Shtalryd et al. | |
| 5,515,865 | A | 5/1996 | Scanlon | |
| 5,555,891 | A * | 9/1996 | Eisenfeld | 600/534 |
| 5,684,460 | A | 11/1997 | Scanlon | |
| 5,853,372 | A * | 12/1998 | Britton | 600/500 |
| 5,913,826 | A * | 6/1999 | Blank | 600/504 |
| 6,011,477 | A * | 1/2000 | Teodorescu et al. | 340/573.1 |
| 6,122,537 | A * | 9/2000 | Schmidt | 600/534 |
| 6,208,897 | B1 * | 3/2001 | Jorgenson et al. | 607/5 |
| 6,816,266 | B2 * | 11/2004 | Varshneya et al. | 356/477 |
| 2004/0111045 | A1 * | 6/2004 | Sullivan et al. | 600/595 |
| 2009/0018409 | A1 * | 1/2009 | Banet et al. | 600/301 |
| 2009/0259135 | A1 * | 10/2009 | Stasz | 600/534 |

* cited by examiner

*Primary Examiner* — Thomas Mullen
(74) *Attorney, Agent, or Firm* — Roman Aguilera, III

(57) ABSTRACT

A non-invasive motion and respiration monitor receives impulses from a subject's movement, heartbeat, and respiration. The raw signal is biased and digitized, and a signal processor applies a Fast Fourier Transform to the signal. The transformed signal is filtered to isolate the component representing heart rate from the component representing respiration. An Inverse Fast Fourier Transform is then applied to the component signals, which are sent to a processor. The processor is programmed to detect irregularities in the respiration and heart rate. If severe irregularities or complete cessation is detected in either signal, a mechanical stimulator is actuated to try to stimulate the subject, and an alarm is sounded to alert a caregiver such as a parent or nurse.

10 Claims, 5 Drawing Sheets

NONINVASIVE MOTION AND RESPIRATION MONITORING SYSTEM

CROSS REFERENCE TO RELATED APPLICATIONS

This application claims priority to U.S. Provisional Application No. 61/195,512, filed Oct. 8, 2008, titled "Noninvasive Movement and Respiration Monitor Utilizing Isolated Array, Analysis, and Alarm and Stimulation."

BACKGROUND

The invention relates to modular, age-scalable, FPGA-controlled, self-centering biasing signal, monitoring devices of cardiovascular and respiratory rhythms of patients and human subjects in general that is suitable for utilization on or incorporated into beds, lying-pads, furniture, vehicles and clothing. Among other applications, the invention enables what can be termed as smart-beds that will also be of interest to hospitals and emergency response vehicles. The device can be used to detect and monitor medical conditions such as SIDS, epilepsy, seizure, and sleep apnea. The self-centering biasing function of the invention described herein eliminates the need to manually reset the monitoring device. In one specific utilization, this invention can be employed for monitoring the respiratory function of infants in slumber, sleeping individuals and patients in health care facilities. For illustration purposes, the rest of the description contained herein will focus on infants in slumber.

Sudden Infant Death Syndrome (SIDS) is the leading cause of death among infants who are one month to one year old, and claims the lives of about 2,500 infants each year in the United States alone. The instant invention offers parents around the globe the opportunity to save their child's life by immediately informing them that a problem exists, as well as triggering an auditory or physical intervention mechanism. Prompt notification reduces response time to seconds; thereby providing parents with the opportunity to take life saving measures. Because of the nature of this invention, this technology is of interest to parents, infant caretakers, health care facilities, retirement homes and medical personnel.

SUMMARY OF THE INVENTION

Figure 1:
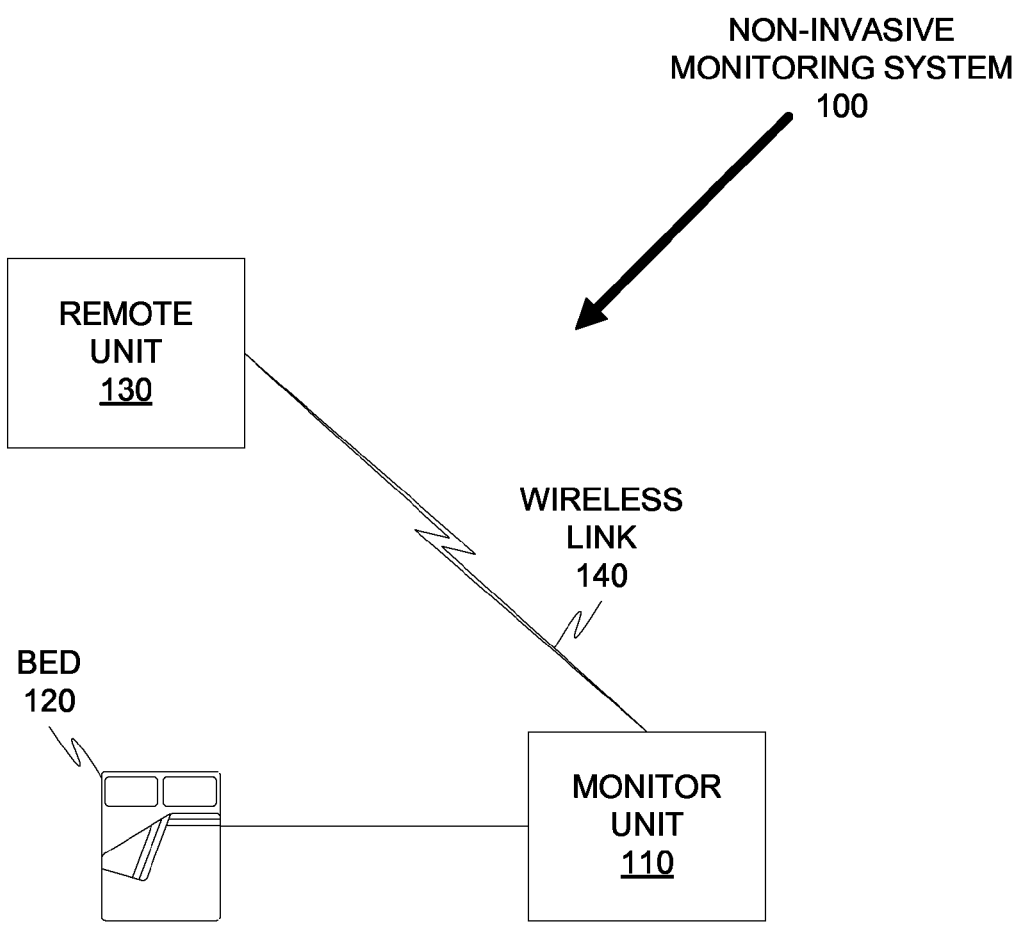
FIG. 1 is a block diagram of an exemplary embodiment of a non-invasive monitoring system.

In one aspect, a non-invasive motion and respiration monitoring system receives impulses from a subject's movement, heartbeat, and respiration. The raw signal is biased and digitized, and a signal processor applies a Fast Fourier Transform to the signal. The transformed signal is filtered to isolate the component representing heart rate from the component representing respiration. An Inverse Fast Fourier Transform is then applied to the component signals, which are sent to a processor. The processor is programmed to detect irregularities in the respiration and heart rate. If severe irregularities or complete cessation is detected in either signal, a mechanical stimulator is actuated to try to stimulate the subject, and an alarm is sounded to alert a caregiver such as a parent or nurse.

DETAILED DESCRIPTION OF THE EMBODIMENTS

A non-invasive motion and respiratory monitoring system monitors cardiovascular and respiratory rhythms of a human subject, for instance, a sleeping or resting child or adult without the use of cumbersome, intrusive or potentially hazardous wires attached to the subject. The respiration may be monitored and analyzed by laying the individual on a mat having transducers disposed thereon. If the breathing patterns and heart beat of the child or adult are detected, a signal indicating the respiratory motion and pulse is wirelessly transmitted through to a receiver. If breathing or the pulse stops or becomes erratic, an audio and/or visual system alerts caretakers or parents of the anomalous situation. The sleeping pad also incorporates a mechanical stimulator, such as a gentle vibration system, within the mat to stimulate the individual if it stops breathing; mimicking a technique utilized by hospital staff in similar situations. Such a monitoring system can therefore be used by parents, infant caretakers, health care facilities, retirement homes and medical personnel to mitigate reduce death or injury from causes such as sudden infant death syndrome (SIDS), sleep apnea, or other similar and possibly-preventable causes.

In an exemplary embodiment, a monitor unit includes a sensor pad that can be placed on a mattress where a subject, such as a baby, is to sleep. The sensor pad may, for example, be placed beneath a fitted sheet, which will keep the sensor in place and not substantially impair its sensitivity. A parent can then place the baby on the mattress for a nap and turn on both the monitor and a remote unit. Under normal conditions, the baby's normal respiration and heart beat patterns will be detected by the sensor pad, and the monitor will send an "OK" signal to the remote receiver unit. But if normal respiration or heart beat stops for a specified time, such as two seconds, the monitor will send an "ALERT" signal to the remote unit. The monitor may also actuate a stimulation aid, such as a gentle agitator or shrill alarm, intended to startle the baby awake and restart natural respiration and heart beat. The ALERT signal will also cause a shrill alarm to sound on the remote unit, alerting the parent to a problem. This gives the parent an opportunity to try to wake the baby and stimulate activity. In some embodiments, the remote unit may also enter an ALERT state if no OK signal is received from the monitor for a specified time period, such as 20 seconds.

A non-invasive motion and respiration monitor will now be described with more particular reference to the attached drawings. Hereafter, details are set forth by way of example to facilitate discussion of the disclosed subject matter. It should be apparent to a person of ordinary skill in the field, however, that the disclosed embodiments are exemplary and not exhaustive of all possible embodiments. Throughout this disclosure, a hyphenated form of a reference numeral refers to a specific instance or example of an element and the un-hyphenated form of the reference numeral refers to the element generically or collectively. Thus, for example, 102-1 may refer to a "pen," which may be an instance or example of the class of "writing implements." Writing implements may be referred to collectively as "writing implements 102" and any one may be referred to generically as a "writing implement 102."

FIG. 1 discloses a block diagram of an exemplary embodiment of a non-invasive monitoring system 100. Monitoring system 100 includes a monitor unit 110 and a remote unit 130 that may be communicatively coupled, for example via wireless link 140. Wireless link 140 may employ any of a number of protocols known in the art, such as radio frequency (RF), WiFi, microwave, or infrared (IR), by way of non-limiting example. Monitor Unit 110 interfaces with a monitoring point such as bed 120. The disclosed configuration enables monitor unit 110 to monitor activity on bed 120 and communicate with remote unit 130 to indicate either normal respiration and heart activity (an OK condition), or an ALERT condition.

Figure 2:
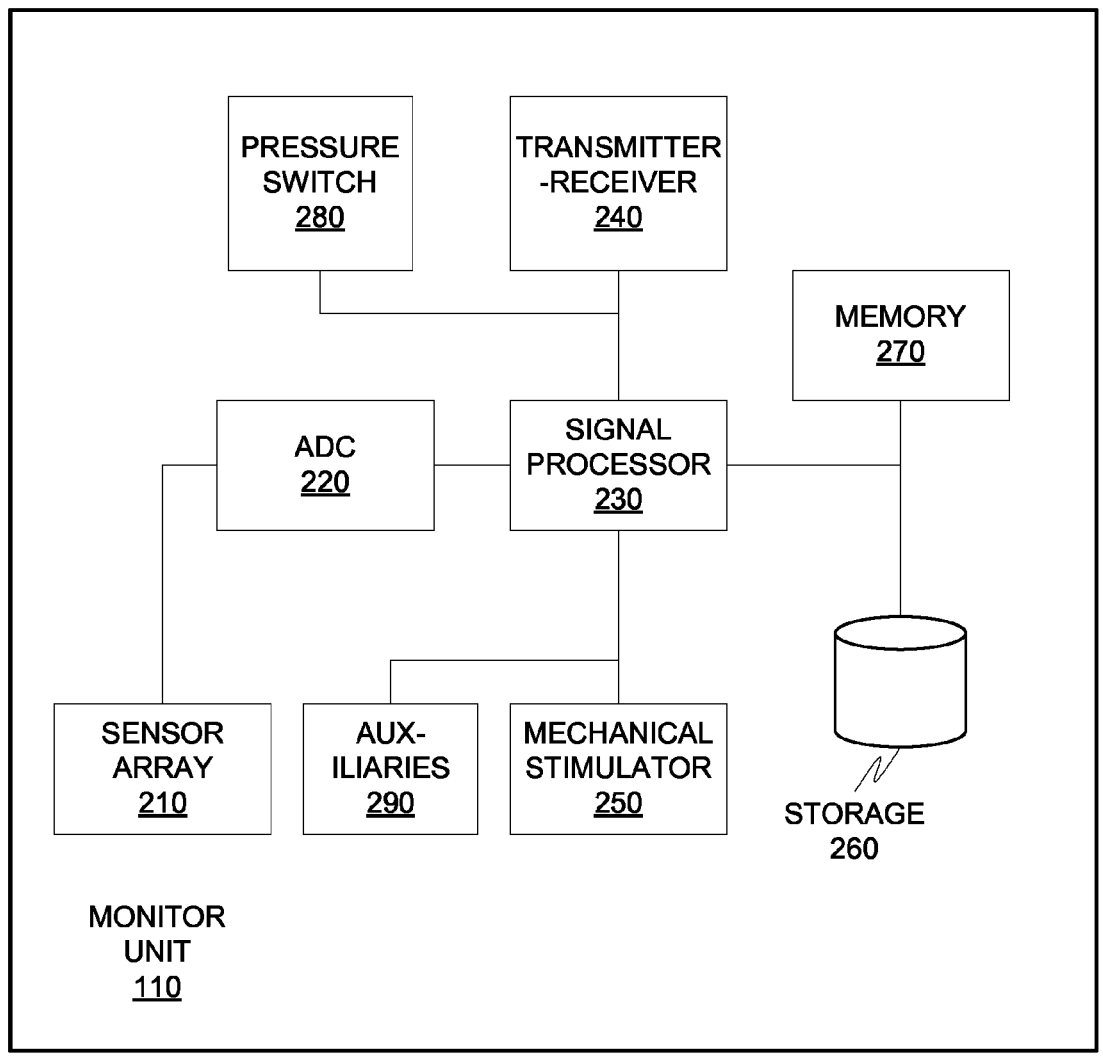
FIG. 2 is a block diagram of an exemplary embodiment of a monitor unit for use with a monitoring system.

FIG. 2 discloses a block diagram of an exemplary embodiment of monitor unit 110. This embodiment includes a sensor array 210, which may include, for example, an array of piezoelectric sensors such as the array disclosed in FIG. 4, or any other suitable impulse-sensitive transducer. Sensor array 210 provides sensitivity over a large surface area. In some embodiments, sensor array 210 may be provided as a single prepared pad constructed of a material selected to not substantially inhibit the sensitivity of the sensors, such as a plastic film. In other embodiments, sensor array 210 may include a pouch filled with a non-conductive fluid, which may translate motion to multiple individual sensors.

Sensor array 210 provides time-domain analog signals to analog-to-digital converter (ADC) 220, which may be one of many such devices known in the art. The purpose of ADC 220 is to receive an analog input signal and to provide a digital output signal. The output from ADC 220 is provided to signal processor 230. In one embodiment, signal processor 230 is a field-programmable gate array (FPGA) programmed to provide suitable functions, such as the process described in FIG. 5. In other embodiments, signal processor 230 may be a processing device such as a microprocessor, microcontroller, digital signal processor, programmable logic array, or similar. Signal processor 230 is also communicatively coupled to a memory 270, which may be a low-latency data medium such as cache or dynamic random access memory (DRAM), or a combination thereof. In some embodiments, memory 270 may be a volatile storage medium, in contrast to storage 260, which may be a similar, but generally higher-latency non-volatile storage medium.

Signal processor 230 is also connected to a mechanical stimulator 250. Mechanical stimulator 250 may be configured, for example, to gently shake the subject being monitored, which may wake the subject or cause him or her to move, thus restarting the respiratory or heartbeat processes. In particular, if the subject is a baby or is prone to apnea, it's possible that he or she may have breathing blocked by a pillow, blanket, or other obstruction. The stimulator may awaken the subject and cause him or her to move away from the obstruction.

Signal processor 230 is also connected to a transceiver 240, which communicatively couples monitor unit 110 to remote unit 130. Transceiver 240 contains the necessary hardware and software functions to implement wireless link 140, thus enabling signal processor 230 to send signals such as OK or ALERT to remote unit 130. In embodiments where auxiliary equipment is provided, transceiver 240 may also provide additional data, such as streamed audio or video data.

In some embodiments, monitor unit 120 may also include auxiliary devices 290 such as a video camera or microphone configured to provide additional information, such as providing an audio or video feed to an observer operating remote unit 130. In such cases, additional equipment for interfacing with auxiliary equipment, such as additional ADCs, signal processing functions, and compression algorithms may also be provided as necessary. As an additional convenience, a pressure switch 280 may also be provided. Pressure switch 280 may for example be configured to close when an infant is placed on the mattress, but not when lighter items such as bedding or stuffed animals are present. When pressure switch 280 is open, signal processor 230 may enter an inactive state where it ceases to monitor for life signs, thus preventing false positives. For example, it may be annoying if a mother is required to turn monitoring system 100 off within two seconds each time she lifts the baby from its bed, or risk being annoyed by a shrill alarm. Similarly, if the mother must remember to activate monitoring system 100 each time she puts the baby down for a nap, she may occasionally forget, thus limiting the effectiveness of the system. With pressure switch 280, the process of enabling and disabling active monitoring can be automated so that the human error element is mitigated.

Figure 3:
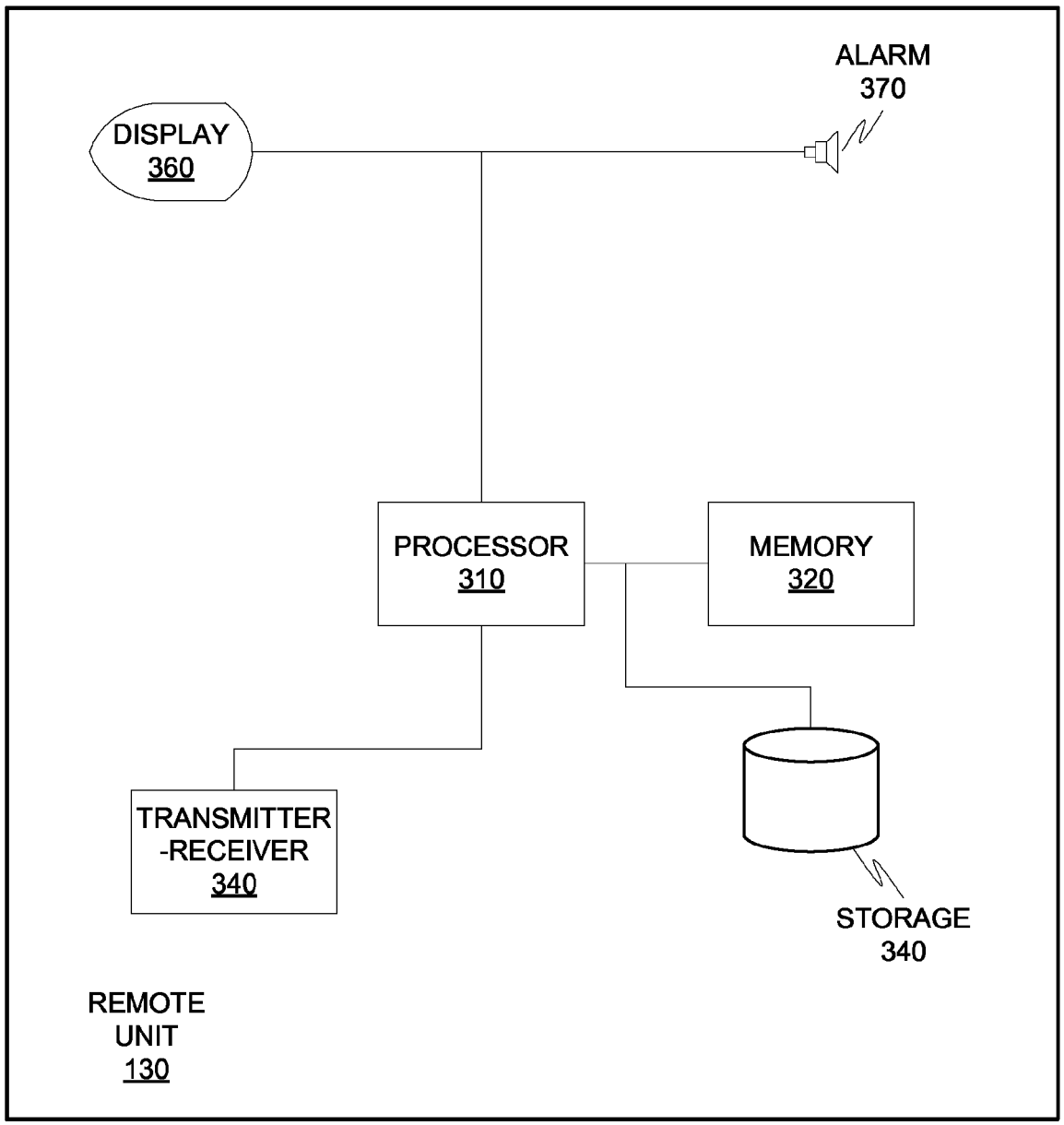
FIG. 3 is a block diagram of an exemplary embodiment of a remote unit for use with a monitoring system.

FIG. 3 is a block diagram of an exemplary embodiment of remote unit 130. Remote unit 130 includes a transceiver 340 configured to communicatively couple remote unit 130 to monitor unit 110. Processor 310 receives data from transceiver 340, including, for example, OK and/or ALERT signals. Processor 310 is also communicatively coupled to a memory 320 and storage 340. These are functionally similar to memory 270 and storage 260 of FIG. 2. Also note that many divisions of processing tasks between processor 310 and signal processor 230 (FIG. 2) are possible without departing from the spirit or scope of the present invention. For example, signal processor 230 may be limited to filtering and transforming digital signals, which may then be sent to processor 310, which in this example would be responsible for providing algorithms to detect irregularities and making decisions on whether to operate in the OK state or ALERT state. In other embodiments, such decision-making algorithms could be provided locally on signal processor 230, which would then be responsible for sending data packets including OK and/or ALERT signals to remote unit 130. In this example, processor 310 of remote unit 130 would simply act on the signal received from signal processor 230 of remote unit 120. For example, processor 310 would take no further action as long as OK signals are regularly received. But in the event that an ALERT signal is received, or that an OK signal is not received for a particular time span, which may for example vary in the range from 5 to 30 seconds, and which may preferably be one of 5, 10, 15, 20, 25, or 30 seconds, then processor 310 may default to an ALERT state. When an ALERT state is entered, processor 310 may activate elements of display 360, such as an audio or video feed, warning LEDs, or other indicators. Processor 310 may also activate alarm 370, which may be a shrill alarm, similar to a fire alarm, configured to command immediate attention.

In the exemplary embodiment, as long as remote unit 130 is operating in the OK state, either no action is taken, or auxiliary actions such as providing an audio or video stream to a display 360 may be performed.

Figure 4:
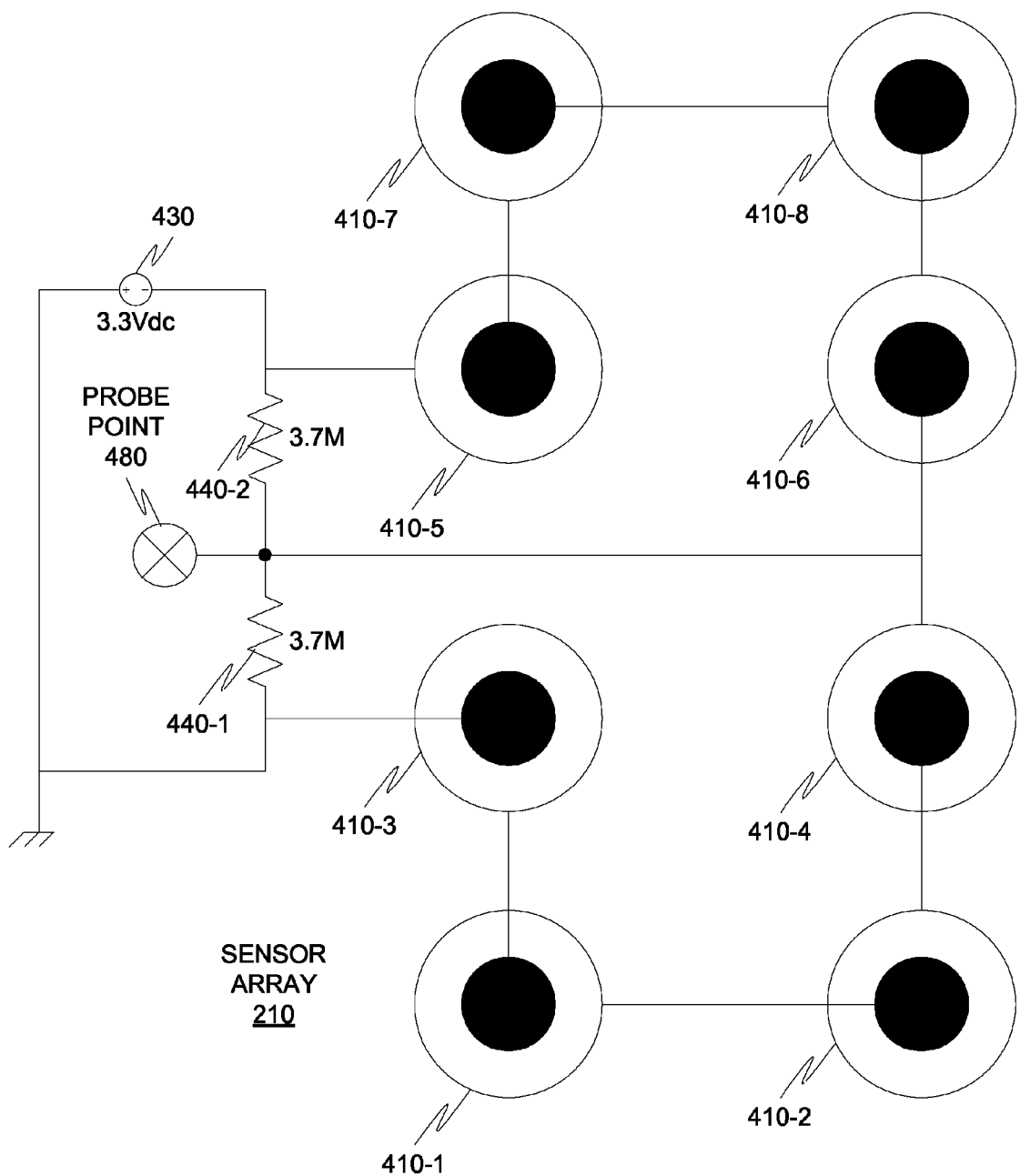
FIG. 4 is a block diagram of an exemplary embodiment of a sensor array for use with a monitoring system.

FIG. 4 is a diagrammatic drawing of sensor array 210. In this exemplary embodiment, sensors 410 may be, for example, piezoelectric sensors such as APS4812B-LW100-R piezoelectric transducers produced by PUI Audio (a division of Products Unlimited). Those having skill in the art will recognize that other impulse-sensitive transducers could also be used. In the disclosed embodiment, sensors 410 are arranged in an array and connected in series, with a total voltage drop of 3.3V across the array. A probe point 480 is also connected between sensor 410-4 and sensor 410-6. This probe point is biased to a self-centering voltage of approximately 1.65V by a voltage divider formed by resistors 440-1 and 440-2, which in the preferred embodiment are both selected to be 3.7 MΩ.

Figure 5:
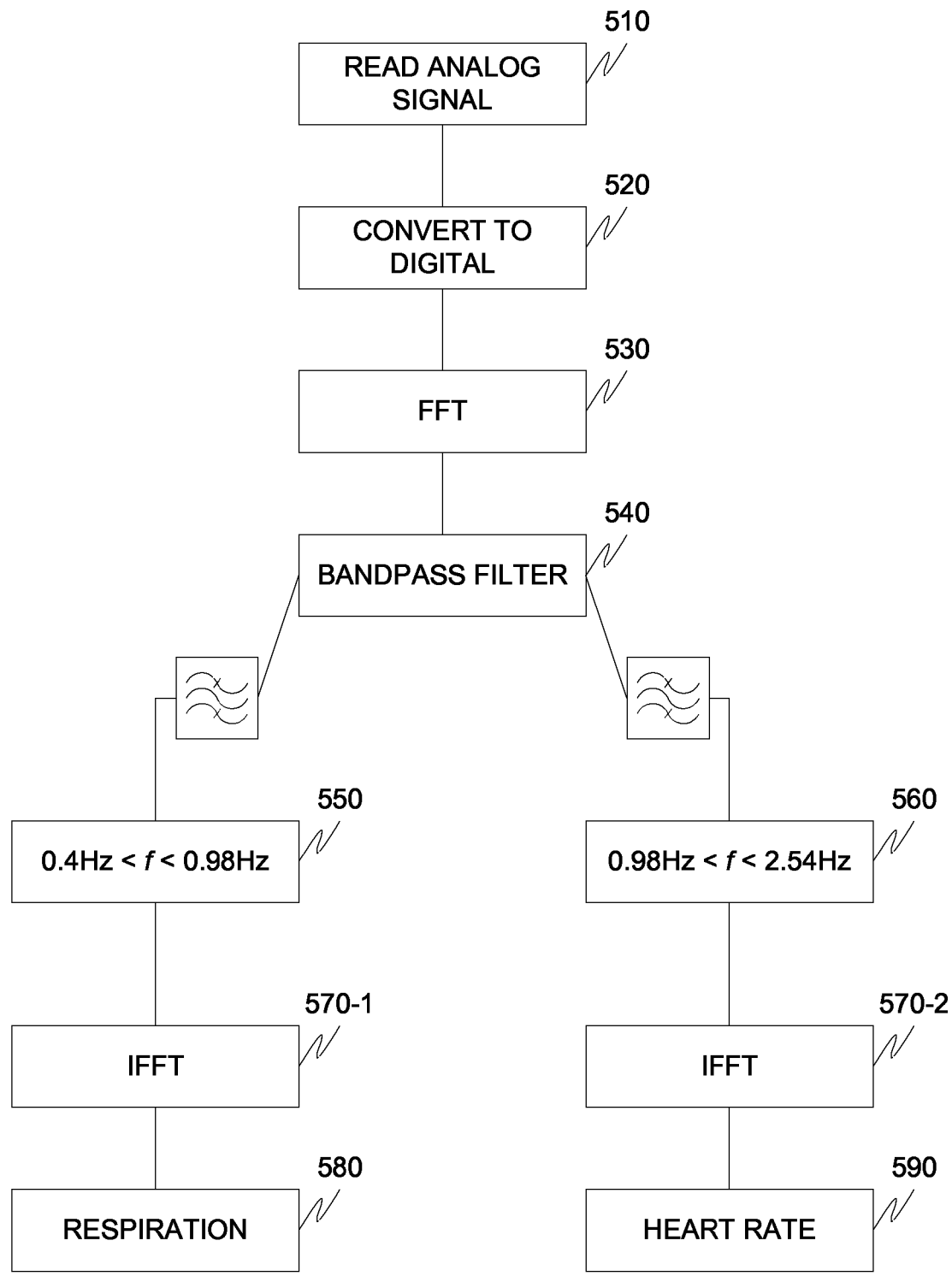
FIG. 5 is a block flow diagram of an exemplary process for monitoring a subject, carried out by a monitoring system.

FIG. 5 is a block diagram of an exemplary process for filtering and detecting a heart rate and respiratory rate. For purposes of discussion, the following description will assume that the process is performed entirely on signal processor 230. But note that the process of FIG. 5 may be performed by signal processor 230 of monitor unit 110, processor 310 of remote unit 130, or tasks may be divided between the two devices without affecting the viability of the process. In the exemplary embodiment, ADC 220 receives a time-domain analog signal from sensor array 210 in block 510. In block 520, ADC 220 converts the analog signal to a time-domain digital waveform, which it provides to signal processor 230. Signal processor 230 performs a Fast Fourier Transform (FFT) on the digitized signal in block 530 to provide a frequency-domain signal, and in block 540 runs the frequency-domain signal through a pair of bandpass filters. In block 550, the first bandpass filter passes frequencies in the range of 0.4 Hz to 0.98 Hz to isolate the portion of the signal representing a respiratory pattern. In block 560, the second bandpass filter passes frequencies in the range from 0.98 Hz to 2.54 Hz to isolate the portion of the signal representing a heart rate. In blocks 570-1 and 570-2, an inverse Fast Fourier Transform (IFFT) is performed on each frequency-domain signal, resulting in two separate time-domain signals, one representing respiration in block 580, and one representing heart rate in 590.

With the signals thus isolated, problems can be detected in as little as two seconds. For example, if the heart rate signal goes flat for two full seconds, this may represent between two and five heart beats missed completely. As missing two to five heart beats can be considered anomalous, monitoring system 100 can enter an ALERT state after 2 seconds with a reduced probability of a false positive. Similarly, if the respiratory signal is flat for a full two seconds, this may represent between one and two breath cycles completely missed. As a normally sleeping baby will not hold its breath for one to two full breathing cycles, this can also be considered an anomalous result, causing monitoring system 100 to enter an ALERT state. Furthermore, if the heart rate or respiration pattern becomes excessively fast and/or shallow, the signal will not pass bandpass filter 540, so that the anomalous result will still be detected.

The occurrence of false positives will vary inversely with the time span selected to represent an anomalous condition. For example, if signal processor 230 waits for five seconds before entering an ALERT state, this may represent between 5 and 13 missed heart beats and between 2 and 5 missed breaths, or alternatively five seconds of irregularly fast respiration and/or heart rate. This is more likely to be an anomalous condition than at two seconds, but also spends an additional three seconds of precious response time. Similarly, at intervals of 10, 15, and 20 seconds, the likelihood of a false positive drops dramatically with the increased time, but time for a parent or care giver to appropriately respond and render aid is increasingly impinged on. In an alternative embodiment, responses to timer intervals can be gradated, so that an increased response can be provided in response to an increased likelihood of a problem. In this embodiment, monitoring system 100 will provide more than just a binary OK/ALERT state. Instead, the OK state may be followed by a number of ALERT grades, such as ALERT0, ALERT1, ALERT2, etc. For example, the ALERT0 stage may be triggered after two seconds. In response to ALERT0, signal processor 230 may gently actuate mechanical stimulator 250 to try to agitate the subject just enough to get a response. If the signal remains flat for an additional 3 seconds, monitoring system may enter ALERT1 state, and in response more aggressively actuate mechanical stimulator 250, as well as light an indicator such as an LED on display 360 of remote unit 130. If no response is received for an additional 2 to 5 seconds, monitoring system 100 may enter an ALERT2 state, and in response continue to aggressively actuate mechanical stimulator 250, as well as sound a shrill audible alarm such as alarm 370.

In use, the mat containing sensor array 210 of monitoring system 100 is placed on a sleeping surface such as bed 120, e.g., a foam mat or mattress, and the mat is covered with either a sheet or additional foam material for comfort. Alternatively, however, sensor array 210 can be integrated into a mattress of bed 120. The electronics are preferably placed outside of the sleeping area, and all wires connecting the transducer electronics and power supplies are secured via e.g., Velcro, to a surface out of the reach of the child/adult to avoid any strangulation risks.

Once sensor array 210 and necessary electronics are in place, a child or adult lays on bed 120 and monitoring system 100 either is automatically powered on, or is turned on by a caregiver.

While the child or adult is lying on bed 120, the monitoring device of the instant invention is constantly monitoring the heart beat and respiratory rate of the child or adult. If the respiratory rate or hear beat becomes erratic or stops, remote unit 130 issues an audio and/or visual alarm to the caregiver so that life saving measures can be administered to the child or adult.

As one skilled in the art will appreciate, several modifications can be made to the above embodiment and such modifications are included within the scope of this disclosure. For example, transceiver 240 of monitor unit 110 could be a one-directional transmitter, while transceiver 340 of remote unit 130 could be a one-directional receiver. With bi-directional communication, however, additional features can be provided, such as allowing a care giver to request an audio or video feed, or manually control mechanical stimulator 250 in the case of SIDS. Remote unit 130 could also receive telemetric data such power status for the transducer array. Additionally, the memory 270 may store multiple life signals for a particular child or adult for wired or wireless upload to a physician computer or hospital network. Also, signal processor 230 and processor 310 may be capable of being reprogrammed or written with multiple programs that a user can toggle between depending upon application. In other words, the monitoring device could be capable of monitoring SIDs, seizure activity and apnea. Furthermore, while heart rate and respiration are disclosed as exemplary embodiments of possible bio-indicators to monitor, those having skill in the art will recognize that other pass bands could be used to isolate and monitor additional bio-indicators.

While the subject of this specification has been described in connection with one or more exemplary embodiments, it is not intended to limit the claims to the particular forms set forth. On the contrary, the appended claims are intended to cover such alternatives, modifications and equivalents as may be included within their spirit and scope.

What is claimed is:

1. A method of non-invasively monitoring heart rate and respiration of an infant for mitigating the risk of sleep apnea comprising the steps of:

receiving a time-domain composite signal from a single impulse-sensitive sensor array comprising impulse-sensitive transducers connected in series so as to reduce dependence of the receiving on the positional placement of the transducers with respect to the body of the infant, the time-domain composite signal comprising a respiration rate component and a heart rate component;

applying a Fast Fourier Transform function to the time-domain composite signal to convert the time-domain composite signal to a frequency-domain composite signal;

filtering the frequency-domain composite signal through a first bandpass filter with a pass band between 0.4 and 0.98 hertz to provide a frequency-domain respiration rate signal and filtering the frequency-domain composite signal through a second bandpass filter with a pass band between 0.98 and 2.54 hertz to provide a frequency-domain heart rate signal;

applying an inverse Fast Fourier Transform function to the frequency-domain respiration rate signal and heart rate signal to provide a time-domain respiration rate signal and time-domain heart rate signal; and providing an alert if either the time-domain heart rate signal or the time-domain respiration rate signal is interrupted for a time span between two and twenty seconds.

2. The method of claim 1 further comprising the step of providing a shrill alarm to the infant upon receiving the alert.

3. The method of claim 1 further comprising the step of automatically gently agitating the infant upon receiving the alert.

4. A non-invasive monitoring system comprising:

a sensor array comprising impulse-sensitive transducers connected in series so as to reduce dependence of a sensing function on the positional placement of the transducers with respect to the body of an infant, the sensor array configured to be disposed adjacent to an infant mattress and to carry out the sensing function by providing a time-domain composite output waveform responsive to the infant's respiration and heart beat;

an infant agitator;

a signal processor configured to:

receive the time-domain composite output waveform;

apply a Fast Fourier Transform to the time-domain composite output waveform to provide a frequency-domain composite waveform;

filter the frequency-domain composite waveform through a first bandpass filter having a pass band between 0.4 and 0.98 hertz to provide a frequency-domain respiration signal, and filter the frequency-domain composite waveform through a second bandpass filter having a pass band between 0.98 and 2.54 hertz to provide a frequency-domain heart rate signal;

apply an inverse Fast Fourier Transform to the frequency-domain respiration signal to provide a time-domain respiration signal, and apply an inverse Fast Fourier Transform to the frequency-domain heart rate signal to provide a time-domain heart rate signal;

upon failing to detect either a time-domain respiration signal or a time-domain heart rate signal for a time period between two and twenty seconds, enter an alert state and activate the infant agitator.

5. The system of claim 4 wherein the sensor array comprises piezoelectric sensors.

6. The system of claim 4 wherein the output of the sensor array is biased to a desired output level by means of a voltage divider.

7. The system of claim 4 wherein:

the sensor array provides the time-domain output waveform to the signal processor by means of an analog-to-digital converter; and the signal processor is a field-programmable gate array configured to receive a digital input signal.

8. The system of claim 4 wherein the infant agitator is a physical agitator configured to gently agitate the mattress to awake the infant.

9. The system of claim 4 wherein the infant agitator is a shrill alarm configured to sit near the mattress.

10. The system of claim 4 further comprising a wireless link to a parental unit, the parental unit configured to:

receive a signal form the alert state; and provide a parental notification alarm.

* * * * *